(12) United States Patent
Weisgarber et al.

(10) Patent No.: US 8,571,667 B2
(45) Date of Patent: Oct. 29, 2013

(54) ACTIVE CURRENT CONTROL USING THE ENCLOSURE OF AN IMPLANTED PULSE GENERATOR

(75) Inventors: Jeff A. Weisgarber, Jewett, OH (US); Stephen C. Trier, Mayfield Heights, OH (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 13/175,283

(22) Filed: Jul. 1, 2011

(65) Prior Publication Data
US 2013/0006331 A1    Jan. 3, 2013

(51) Int. Cl.
*A61N 1/36* (2006.01)

(52) U.S. Cl.
USPC .......................................................... 607/46

(58) Field of Classification Search
USPC ................................................. 607/46, 55–57
See application file for complete search history.

(56) References Cited

U.S. PATENT DOCUMENTS

| | | | |
|---|---|---|---|
| 5,895,416 A | 4/1999 | Barreras, Sr. et al. | |
| 6,181,969 B1 * | 1/2001 | Gord | 607/59 |
| 6,219,580 B1 * | 4/2001 | Faltys et al. | 607/57 |
| 6,393,325 B1 * | 5/2002 | Mann et al. | 607/46 |
| 6,516,227 B1 | 2/2003 | Meadows et al. | |
| 6,553,263 B1 | 4/2003 | Meadows et al. | |
| 6,895,280 B2 | 5/2005 | Meadows et al. | |
| 7,444,181 B2 * | 10/2008 | Shi et al. | 607/2 |
| 7,496,404 B2 | 2/2009 | Meadows et al. | |
| 7,622,988 B2 | 11/2009 | Denison et al. | |
| 7,747,318 B2 | 6/2010 | John et al. | |
| 7,769,462 B2 | 8/2010 | Meadows et al. | |
| 7,801,615 B2 | 9/2010 | Meadows et al. | |
| 7,805,197 B2 * | 9/2010 | Bradley | 607/46 |
| 7,831,307 B1 * | 11/2010 | Moffitt | 607/46 |
| 2001/0031909 A1 * | 10/2001 | Faltys et al. | 600/25 |
| 2005/0267546 A1 | 12/2005 | Parramon et al. | |
| 2007/0156203 A1 | 7/2007 | Varrichio et al. | |
| 2008/0269630 A1 | 10/2008 | Denison et al. | |
| 2009/0082691 A1 | 3/2009 | Denison et al. | |

(Continued)

FOREIGN PATENT DOCUMENTS

| WO | WO 00/00251 | 1/2000 |
|---|---|---|
| WO | WO 2007/127443 A2 | 11/2007 |

(Continued)

OTHER PUBLICATIONS

European Search Report in European Application No. 12173231.7, mailed Oct. 15, 2012, 6 pages.
European Search Report in European Patent Application No. 12166020.3, dated Sep. 27, 2012, 5 pages.

*Primary Examiner* — George Evanisko
(74) *Attorney, Agent, or Firm* — Haynes and Boone, LLP

(57) ABSTRACT

An electrical stimulation apparatus including a medical device. The medical device includes: a housing component having at least one electrically conductive area. The medical device includes a plurality of conductors configured to be electrically coupled to a distal electrode array. The electrode array are implantable in a human body. The medical device includes a stimulation circuit positioned inside the housing component. The stimulation circuit includes a plurality of controllable stimulation channels. A first subset of the stimulation channels is electrically coupled to the conductors. A second subset of the stimulation channels is electrically coupled to the electrically conductive area of the housing component. The stimulation circuit is operable to simultaneously create a first stimulation path in the electrode array and a second stimulation path that extends from the electrode array to the housing component.

42 Claims, 10 Drawing Sheets

(56) References Cited

U.S. PATENT DOCUMENTS

| | | |
|---|---|---|
| 2010/0069768 A1 | 3/2010 | Min et al. |
| 2010/0114202 A1 | 5/2010 | Donofrio et al. |
| 2010/0204766 A1 | 8/2010 | Zdeblick et al. |
| 2010/0280577 A1 | 11/2010 | Roy et al. |
| 2012/0277822 A1 | 11/2012 | Trier |
| 2012/0296391 A1 | 11/2012 | Trier et al. |

FOREIGN PATENT DOCUMENTS

| | | |
|---|---|---|
| WO | WO 2010/033610 A1 | 3/2010 |
| WO | WO-2010/055421 | 5/2010 |
| WO | WO 2010/065761 A2 | 6/2010 |
| WO | WO 2011/014909 A1 | 2/2011 |
| WO | WO 2012/088482 A1 | 6/2012 |

* cited by examiner

ACTIVE CURRENT CONTROL USING THE ENCLOSURE OF AN IMPLANTED PULSE GENERATOR

BACKGROUND

As medical device technologies continue to evolve, neurostimulator devices have gained much popularity in the medical field. Neurostimulator devices include battery-powered or battery-less devices that are designed to deliver electrical stimulation to a patient. Through proper electrical stimulation, the neurostimulator devices can provide pain relief for patients.

Conventional neurostimulator devices may use a conductive enclosure to hermetically seal various components of the neurostimulator device therein. Such enclosure may be used to passively sink or source stimulation current in concert with a plurality of distal electrodes. For example, when a neurostimulator device operates in a monopolar mode, all of the activated distal electrodes (i.e., electrodes that are "turned on") are driven with the same polarity while the enclosure is of the opposite polarity. As another example, when the neurostimulator device operates in a bipolar mode, the activated distal electrodes are programmed with either positive or negative polarity, and the enclosure is not used to sink or source any of the current. In other words, all current is sourced and sunk at the distal electrodes, and no current passes through the enclosure in the bipolar mode of operation. However, in these conventional neurostimulator devices, the enclosure itself is not programmable and cannot function as a controlled source of current in either the monopolar or the bipolar mode of operation. Such limitation may diminish the effectiveness and the flexibility of conventional neurostimulator devices.

Therefore, although existing neurostimulator devices have been generally adequate for their intended purposes, they have not been entirely satisfactory in every aspect.

SUMMARY

One of the broader forms of the present disclosure involves a method. The method includes: providing a neurostimulator that includes a stimulation circuit, an enclosure housing the stimulation circuit therein, the enclosure having at least one conductive area, and a plurality of distal electrodes coupled to the stimulation circuit through the enclosure; operating the stimulation circuit to energize a first subset of the distal electrodes with a first polarity; operating the stimulation circuit to energize a second subset of the distal electrodes with a second polarity opposite the first polarity, the second subset being different from the first subset; and operating the stimulation circuit to energize the enclosure with one of the first and second polarities.

Another one of the broader forms of the present disclosure involves a neurostimulation medical system. The neurostimulation medical system includes: a controller circuit configured to generate control signals in response to external programming signals; a stimulation circuit configured to generate stimulation signals in response to the control signals; a plurality of implantable electrodes; a plurality of conductors configured to deliver the stimulation signals from the stimulation circuit to the electrodes; and an enclosure that houses the controller circuit and the stimulation circuit therein, the enclosure containing an area that is electrically conductive; wherein the stimulation circuit is configured to activate a first subset of the electrodes to a first polarity, a second subset of the electrodes to a second polarity, and the enclosure to one of the first and second polarities, so as to cause a first stimulation path to be formed between at least one of the electrodes in the first subset and at least one of the electrodes in the second subset, and a second stimulation path to be formed between the enclosure and at least one of the electrodes in the first and second subsets.

Yet another one of the broader forms of the present disclosure involves a medical device. The medical device includes: a housing component having at least one electrically conductive area; a plurality of conductors configured to be electrically coupled to a distal electrode array, the electrode array being implantable in a human body; and a stimulation circuit positioned inside the housing component; wherein: the stimulation circuit includes a plurality of controllable stimulation channels, a first subset of the stimulation channels being electrically coupled to the conductors, and a second subset of the stimulation channels being electrically coupled to the electrically conductive area of the housing component; and the stimulation circuit is operable to simultaneously create a first stimulation path in the electrode array and a second stimulation path that extends from the electrode array to the housing component.

One more of the broader forms of the present disclosure involves an electrical stimulation apparatus. The electrical stimulation apparatus includes: a stimulation circuit containing a plurality of current sources, wherein at least a subset of the current sources each include at least one adjustable electrical supply; an enclosure housing the stimulation circuit, the enclosure having at least one electrically conductive portion; and a lead wire coupling assembly for electrically coupling the stimulation circuit to one or more distal electrodes; wherein at least one of the current sources in the subset is electrically coupled to the electrically conductive portion of the enclosure.

Another one of the broader forms of the present disclosure involves a method of controlling a neurostimulator. The method includes: providing a neurostimulator that includes a stimulation circuit, an enclosure surrounding the stimulation circuit, and a plurality of lead wires coupled to the stimulation circuit through the enclosure, wherein the enclosure includes at least one conductive area, and wherein the lead wires are configured to provide electrical pulses generated by the stimulation circuit to a remote electrode array; receiving control signals from outside the enclosure; and in response to the control signals, controlling the stimulation circuit to cause a first stimulation path to be formed within the remote electrode array and to cause a second stimulation path to be formed from the remote electrode array to the enclosure.

Yet another one of the broader forms of the present disclosure involves an electrical stimulation device. The electrical stimulation device includes: stimulation means for generating signals that can stimulate a body tissue, wherein the stimulation means include one or more adjustable electrical supply means; enclosure means for housing the stimulation means, the enclosure means having at least one electrically conductive portion; and coupling means for electrically coupling the stimulation means to one or more distal electrodes; wherein the stimulation means is configured to simultaneously drive the enclosure through the conductive portion and drive at least a subset of the distal electrodes.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Figure 1:
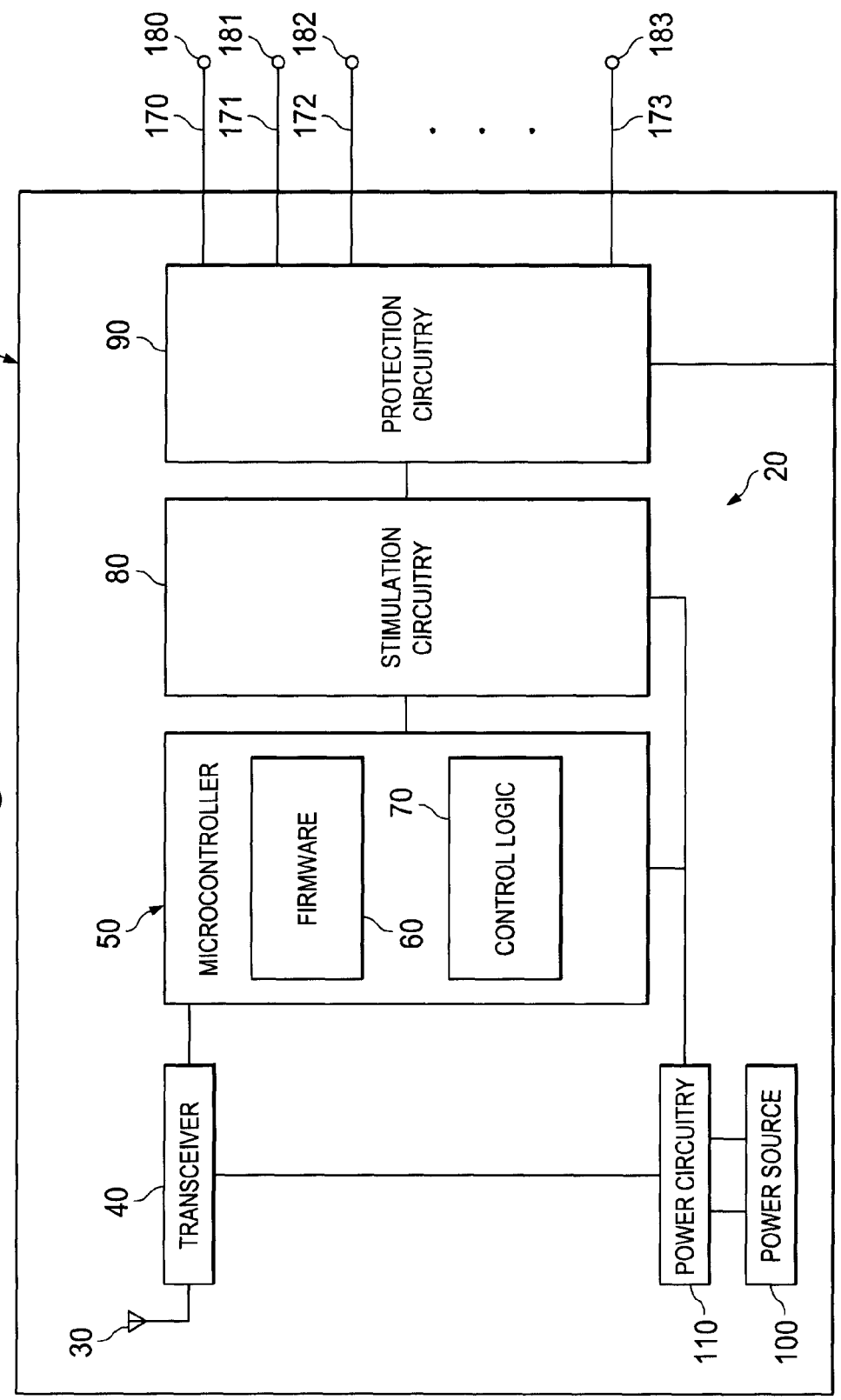
FIG. 1 is a simplified diagrammatic view of an embodiment of a neurostimulator device.

FIG. 1 is a simplified diagrammatic view of an embodiment of a neurostimulator device 20. The neurostimulator device 20 includes an antenna 30 and a transceiver 40 coupled to the antenna 30. The antenna 30 is capable of sending signals to an external device and receiving signals from the external device. The transceiver 40 contains transmitter circuitry and receiver circuitry that together carry out digital communication with the external device. In an embodiment, the signals are transmitted and received at Radio Frequencies (RF).

The neurostimulator device 20 includes a microcontroller 50 that is coupled to the transceiver 40. Based on the output of the transceiver 40 (i.e., the input received from the external device), the microcontroller 50 runs firmware 60, which is a control program, to operate control logic 70. The firmware 60 includes dedicated low-level software code that is written for a specific device, in this case the control logic 70. The control logic 70 includes digital circuitry that is implemented using a plurality of transistors, for example Field Effect Transistors (FETs). In the embodiment shown in FIG. 1, the firmware 60 and the control logic 70 are integrated into the microcontroller 50. In alternative embodiments, the firmware 60 or the control logic 70 may be implemented separately from the microcontroller 50.

The neurostimulator device 20 includes stimulation circuitry 80 that receives the output of the microcontroller 50. In an embodiment, the stimulation circuitry 80 is implemented on an Application Specific Integrated Circuit (ASIC) chip. The stimulation circuitry 80 includes electrical pulse generation circuitry. Based on the output of the microcontroller 50, the electrical pulse generation circuitry generates electrical pulses (signals) to a target tissue area. Various aspects of the pulse generation are described in detail in U.S. patent application Ser. No. 13/081,896, Titled "Charge Balancing For Arbitrary Waveform Generator & Neural Stimulation Application" and filed on Apr. 7, 2011, U.S. patent application Ser. No. 13/082,097, Titled "Arbitrary Waveform Generator & Neural Stimulation Application With Scalable Waveform Feature" and filed on Apr. 7, 2011, and U.S. patent application Ser. No. 13/081,936, Titled "Arbitrary Waveform Generator & Neural Stimulation Application" and filed on Apr. 7, 2011, each of which is hereby incorporated by reference in its entirety. Other aspects of the stimulation circuitry 80 will be discussed later in greater detail.

The neurostimulator device 20 also includes protection circuitry 90 that is coupled to the output of the stimulation circuitry 80. In an embodiment, the protection circuitry 90 includes direct-current (DC) blocking capacitors and other electrical transient suppression components. The protection circuitry 90 protects the patient's tissue from unwanted electrical signals. The protection circuitry 90 also protects the neurostimulator device 20 from undesirable external events such as electrostatic discharge, defibrillation, or electrocautery.

The neurostimulator device 20 also includes a power source 100 and power circuitry 110. In an embodiment, the power source 100 includes a battery. In another embodiment, the power source 100 includes a coil that is a part of a transformer (not illustrated). In that case, the transformer has a charging coil that is external to the neurostimulator device 20 and inductively coupled to the coil of the power source 100. The power source 100 therefore obtains energy from such inductive coupling to the charging coil. In some embodiments, the power source 100 may also include both a battery and a coil. The power source 100 provides electrical power to the power circuitry 110. The power circuitry 110 is coupled to the transceiver 40, the microcontroller 50, and the stimulation circuitry 80. The power circuitry 110 supplies and regulates power to these coupled circuitries. In an embodiment, the power circuitry 110 is implemented on an ASIC device.

In an embodiment, the antenna 30, the transceiver 40, the microcontroller 50, the stimulation circuitry 80, the protection circuitry 90, the power source 100, and the power circuitry 110 may be collectively viewed as a stimulation circuit (or components of the stimulation circuit) and are all contained within a hermetically-sealed enclosure 150 (which may also be referred to as a can or a housing). The enclosure 150 may also be considered a part of the neurostimulator device 20. The enclosure 150 may be made from titanium or another suitable biocompatible, durable, and/or conductive material. According to various aspects of the present disclosure, the enclosure 150 is also electrically coupled to the stimulation circuitry 80 through the protection circuitry 90, in a manner such that the stimulation circuitry can drive the enclosure 150 with an electrical supply such as a current sink or a current source. The enclosure 150 and the manner in which it is driven will be discussed in more detail below in association with other Figures.

Still referring to FIG. 1, a plurality of conductors run from the internal circuitry through hermetic feedthroughs to one or more connectors (also referred to as headers) mounted on the enclosure 150. The lead wires 170-173 plug into, and are removable from, those connectors. In another embodiment, the connectors are eliminated, and the lead wires 170-173 are directly and permanently connected to the hermetic feedthroughs. In some embodiments, the neurostimulator device 20 incorporates the electrode contacts into its outer surface. In such embodiments, the hermetic feedthroughs may be designed to incorporate an electrode contact in the tissue-facing side of each feedthrough, or may be designed to have insulated lead wires built into the neurostimulator housing, exterior to the hermetically-sealed enclosure 150, that carry signals between the hermetic feedthroughs and the electrode contacts. It is understood that the lead wires 170-173 are shown merely as examples, and that an alternative number of lead wires may be implemented, for example 16 or 24 lead wires.

Electrode contacts 180-183 (also referred to as electrodes) are coupled to the lead wires 170-173. The electrode contacts 180-183 are implanted in different areas of a patient's body, where electrical stimulation is desired. According to various aspects of the present disclosure, an exterior conductive portion of the enclosure 150 is also used as an electrode contact. This will be discussed in more detail below. In any case, the electrode contacts 180-183 may also be considered parts of the neurostimulator system.

In an embodiment, the neurostimulator device 20 is implemented as an Implanted Pulse Generator (IPG) device, in which case all of the components shown in FIG. 1 are surgically implanted inside the patient's body. Outside the body, the neurostimulator device 20 can be programmed using a Clinician Programmer (not illustrated) or a Patient Programmer (not illustrated). The Clinician Programmer is used by medical personnel (such as doctors or nurses) or by others (such as sales representatives or the patient himself) to configure the neurostimulator device 20 for the particular patient and to define the particular electrical stimulation therapy to be delivered to the target area of the patient's body. The Patient Programmer is used by the patient himself to control the operation of the neurostimulator device 20. For example, the patient can alter one or more parameters of the electrical stimulation therapy, depending on the programming and the configuration of the neurostimulator device 20 as set by the Clinician Programmer.

A medical device manufacturer may manufacture and provide the neurostimulator device 20 to a clinician or a patient. Clinicians may also provide the neurostimulator device to a patient. Some of the functionalities of the microcontroller 50 may be pre-programmed by the manufacturer or may be programmed by the clinician or patient.

Figure 2:
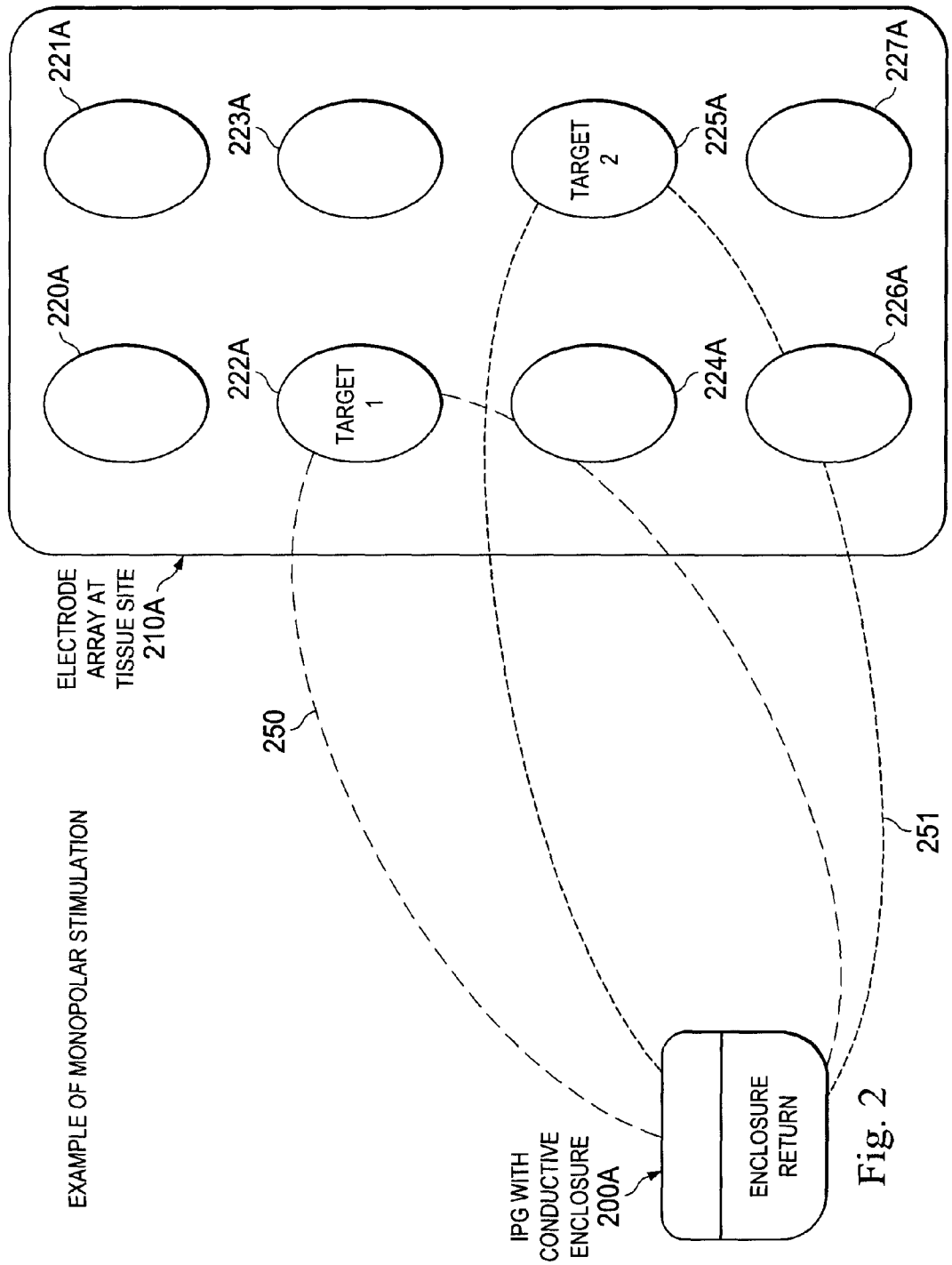
FIG. 2 is a diagrammatic view of an enclosure and an electrode array in a monopolar mode of operation.
Figure 3:
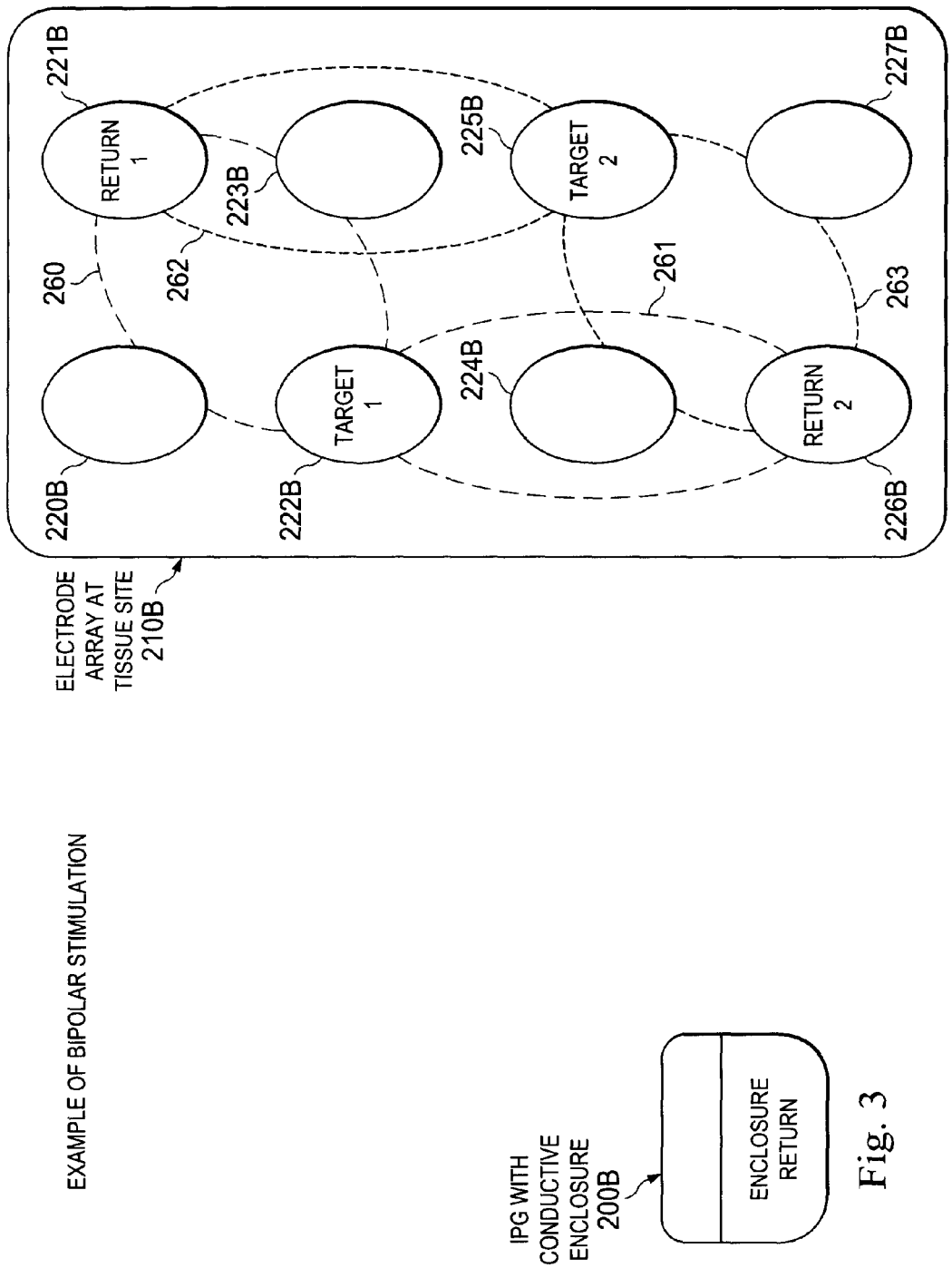
FIG. 3 is a diagrammatic view of an enclosure and an electrode array in a bipolar mode of operation.

Conventional neurostimulator devices typically operate in either a monopolar mode of stimulation or a bipolar mode of operation. In the monopolar mode, all of the activated distal electrodes are driven with the same polarity while the enclosure is of the opposite polarity. In the bipolar mode, the distal electrodes are driven with either positive or negative polarity, and the enclosure is not used to sink or source any of the current. In other words, all current is sourced and sunk at the distal electrodes, and no current passes through the enclosure in the bipolar mode of operation. FIGS. 2 and 3 are provided herein to illustrate the monopolar mode and bipolar mode of operation in more graphical detail.

FIG. 2 is a diagrammatic view of an enclosure 200A and a distal electrode array 210A in a monopolar mode of operation. The enclosure 200A and the electrode array 210A are parts of a neurostimulator device similar to the neurostimulator device 20 of FIG. 1. For example, the enclosure 200A is similar to the enclosure 150 of the neurostimulator device 20, which may be a hermetically-sealed "can" or housing that surrounds the various components of the neurostimulator device 20. At least a portion of the enclosure 200A is conductive. The enclosure 200A is typically implanted inside a patient's body, though away from the nerve tissues that need to be stimulated.

The distal electrode array 210A is typically implanted at or near the nerve tissues intended for stimulation, for example nerve tissues along a segment of a spinal cord. The electrode array 210A contains a plurality of distal electrodes. For the sake of providing an example, electrodes 220A-227A are shown in FIG. 2, though it is understood that the type, number, size, and geometric arrangement of electrodes may differ in other embodiments. In response to the commands received from a Clinician Programmer or a Patient Programmer, the microcontroller 50 (FIG. 1) can selectively "turn on" a subset (or all) of the electrodes 220A-227A. These "turned-on" electrodes may also be referred to as activated electrodes, or may be said to have been energized. Activated or energized electrodes may either sink current (cathode electrode) or source current (anode electrode). It may be said that the current-sinking electrodes and the current-sourcing electrodes have opposite polarities.

The current-sinking current electrodes provide neural stimulation to nearby tissues, and the current-sourcing electrodes provide return paths for the current sunk by the current-sinking electrodes. Thus, in FIGS. 2-4, the current-sinking electrodes are labeled with "Target," and the current-sourcing electrodes are labeled with "Return." In the example monopolar stimulation configuration shown in FIG. 2, electrodes 222A and 225A are current-sinking electrodes. The rest of the electrodes in the electrode array 210A are programmed to be inactive. The currents sunk by the electrodes 222A and 225A are returned by the enclosure 200A. In other words, the enclosure 200A is driven with a polarity opposite from that of the target current-sinking electrodes 222A and 225A. It is understood that the polarities for the enclosure 200A and the electrodes 222A and 225A may switch, so that the enclosure 200A becomes a target electrode and sinks current, while the electrodes 222A and 225A become return path electrodes and source current.

Still referring to FIG. 2, the current flow between the enclosure 200A and the electrodes 222A and 225A create stimulation paths (also referred to as stimulation fields or stimulation regions) 250 and 251, respectively. In an embodiment, each stimulation path is a current path. The stimulation path 250 stretches from the electrode 222A to the enclosure 200A, and the stimulation path 251 stretches from the electrode 225A to the enclosure 200A. In the embodiment shown, the stimulation paths 250-251 each have a three-dimensional oval/elliptical geometry since the body tissue behaves as a volume conductor, but it is understood that stimulation paths may have other geometries or shapes in alternative embodiments. The stimulation paths 250-251 may also partially overlap with one another, as illustrated in FIG. 2. Nerve tissues covered by the stimulation paths 250-251 are being stimulated when the neurostimulator is in operation. The stimulation intensity generally increases along the stimulation paths 250-251 toward the stimulation target electrodes 222A or 225A. Stated differently, nerve tissues near the electrodes 222A or 225A may experience stronger stimulation than nerve tissues near the enclosure 200A.

FIG. 3 is a diagrammatic view of an enclosure 200B and an electrode array 210B in a bipolar mode of operation. In the bipolar mode, the enclosure 200B is inactive, the distal electrodes on the electrode array 210B can be programmed to either sink current (Stimulation target electrode) or source current (Return electrode), but the enclosure 200B is not used to either sink or source any of the current. As an example, FIG. 3 shows the electrodes 222B and 225B as the current-sinking electrodes, and shows the electrodes 221B and 226B as the current-sourcing electrodes. The electrodes 221B and 226B each return current for the stimulation target electrode 222B as well as for the stimulation target electrode 225B. Consequently, stimulation paths 260 and 261 are created between the electrodes 222B-221B and the electrodes 222B-226B, respectively, and stimulation paths 262 and 263 are created between the electrodes 225B-221B and the electrodes 222B-226B, respectively. There may be partial overlapping between these stimulation paths, such as between stimulation paths 260-261 and between stimulation paths 262-263.

Compared to the monopolar stimulation mode shown in FIG. 2, the bipolar stimulation mode shown in FIG. 3 may have shorter stimulation paths, since the stimulation paths are typically confined within the electrode array 210B, as opposed to extending all the way to the enclosure 200B. The shorter stimulation paths may correspond to greater stimulation intensities in regions covered by the stimulation paths.

Operation of the neurostimulator in a strictly monopolar mode or in a strictly bipolar mode each entail shortcomings. For example, in the monopolar mode of operation, all the current sunk by the activated electrodes have to be returned by the enclosure. As a result, the enclosure may be sourcing more current than desirable. The high current density near the enclosure may cause the patient to feel discomfort or even pain at the site of the enclosure, which ideally should have been prevented. As another example, in the bipolar mode of operation, nerve tissues have to reside within a programmed stimulation path to be adequately stimulated. However, electrodes may not be precisely placed during surgery and may migrate after implantation, which would alter the position of the intended stimulation path. Consequently, the target nerve tissues could fall outside of the stimulation path and therefore may not be optimally stimulated.

There are also other disadvantages associated with operating the neurostimulator in a strictly monopolar mode or in a strictly bipolar mode, but these disadvantages are not discussed here for the sake of simplicity. Further, some conventional neurostimulator devices may change the operation mode from monopolar to bipolar (or vice versa) from pulse to pulse, but each pulse is still either fully monopolar or fully bipolar. In any case, conventional neurostimulator devices do not offer the capability to operate a neurostimulator in a "mixed" mode that is a combination (or a superposition) of the monopolar and the bipolar mode in any given individual pulse.

Figure 4:
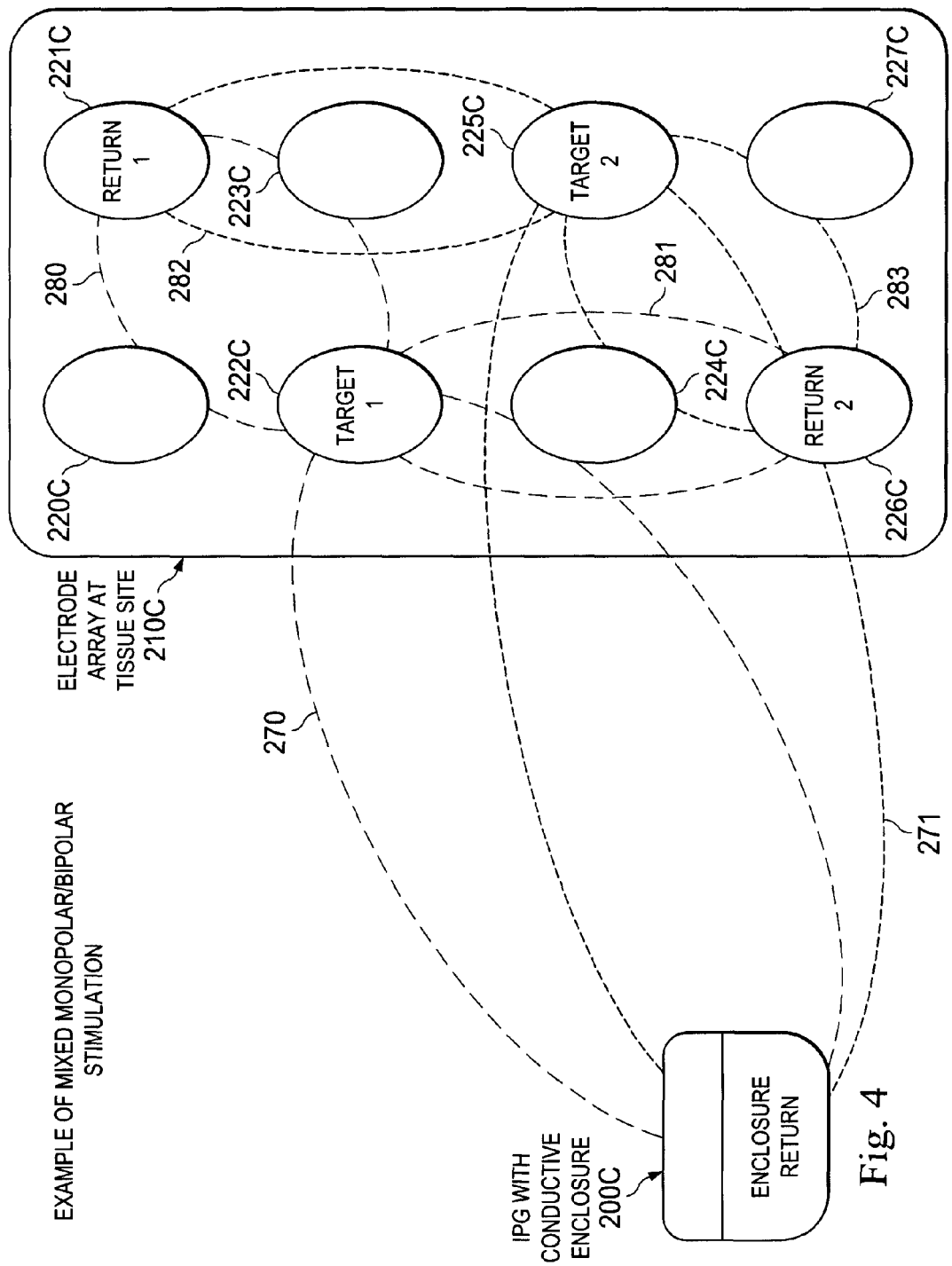
FIG. 4 is a diagrammatic view of an enclosure and an electrode array in a mixed mode of operation.

FIG. 4 is a diagrammatic view of an enclosure 200C and an electrode array 210C in a mixed mode (may also be referred to as a dual mode) of operation. The mixed mode of operation is a combination or a superposition of the monopolar mode and the bipolar mode of operation. In other words, the neurostimulator is being operated in the monopolar mode and the bipolar mode simultaneously, and within any given pulse. In more detail, in the electrode array 210C shown in FIG. 4 (illustrated purely as an example), the electrodes 222C and 225C are programmed as stimulation target electrodes that sink electrical current, while the electrodes 221C and 226C are programmed as return path electrodes that source electrical current. The rest of the electrodes 220C, 223C, 224C, and 227C are inactive.

Meanwhile, the enclosure 200C is also sourcing a portion of the current sunk by the stimulation target electrodes. As such, similar to the electrodes 221C and 226C, the enclosure 200C is in effect serving as a return path electrode, even though it is not a distal electrode itself. In other words, an additional stimulation channel is created by activating the enclosure 200C and using it as a return path electrode. It is also understood that the enclosure 200C may be used to sink current as well, thereby functioning as a target electrode.

In the manner described above, the present disclosure offers M stimulation channels and N distal electrodes (e.g, electrodes that are implemented on the electrode array), where M and N are both integers, and where M is greater than N. For example, in an embodiment, M=N+1. In other embodiments, M may be greater than N by a different number, for example 2, 3, or 4, etc. In some embodiments, M represents the number of active stimulation channels (i.e., channels that are sourcing or sinking current), and N represents the activated distal electrodes (i.e., a cathode or an anode, or a target electrode or a return electrode), wherein M is still greater than N.

In the mixed mode of operation shown in FIG. 4, stimulation paths 270 and 271 are created between the enclosure 200C and the electrodes 222C and 225C, respectively. Meanwhile, stimulation paths 280, 281, 282, and 283 are also created between the electrodes 222C and 221C, 222C and 226C, 225C and 221C, and 225C and 226C, respectively. These stimulation paths 270-271 and 280-283 simultaneously exist and may at least partially overlap with one another.

Thus, in the mixed mode of operation illustrated in FIG. 4, the enclosure 200C functions as an active, rather than passive, electrode. The enclosure is programmable in a substantially similar manner as the rest of the output channels used to drive the distal electrodes. For any given stimulation pulse, current can be distributed between the enclosure 200C and the rest of the distal electrodes as desired by the programmer (e.g., physician or patient). Such mixed mode operation employed by the neurostimulator herein offers many advantages over existing monopolar-only or bipolar-only neurostimulators. It is understood, however, that other embodiments may offer different advantages, and that no particular advantage is required for all embodiments.

One advantage offered by the mixed mode is optimal utilization of the enclosure 200C's high current density limits. Although not readily apparent in FIG. 4—since FIG. 4 is not drawn in scale—the electrodes 220C-227C on the electrode array 210C may vary from one another in size and geometry, as discussed above. The size and/or geometry of each electrode may determine how much current it can sink or source before causing tissue damage. Typically, an electrode with a larger surface area can source or sink a greater amount of current than an electrode with a smaller surface area, as tissue damage is correlated with current density (e.g., measured by current-per-square-inch). Thus, a potential problem may arise due to possible variations of the activated electrodes' surface areas.

To illustrate the problem with an example, suppose the target electrodes 222C and 225C are relatively large electrodes, and the return path electrodes 221C and 226C are relatively small electrodes with smaller surface areas than the electrodes 222C and 225C. The electrodes 222C are each sinking 15 milli-amperes (mA) of current (which may be the maximum amount of current for a given channel according to an embodiment). Thus, the collective amount of current sunk is 30 mA, which means the electrodes 221C and 226C collectively need to source 30 mA of current. However, due to the smaller surface areas, the electrodes 221C and 226C are unable to handle (source) that much current. In a conventional neurostimulator operating under a strictly bipolar stimulation mode, the reduced current handling capability of the electrodes 221C and 226C effectively places an upper limit as to the amount of current that can be sunk by the electrodes 222C and 225C. As a result, the reduced current sunk by the target electrodes 222C and 225C may not provide a sufficient amount of stimulation to a patient.

In comparison with the distal electrodes, the enclosure 200C may include a large conductive surface area and thus can handle a greater amount of current without causing tissue damage. Under the mixed mode of operation, the enclosure 200C may be used to source the excess amount of current that the electrodes 221C and 226C cannot handle. For instance, if the electrodes 221C and 226C can only source 10 mA of current collectively, but 30 mA of current needs to be sunk, then the enclosure 200C can source the remaining 20 mA of current. In this manner, the neurostimulator operating in the mixed mode can still provide a desired amount of current to the stimulation target electrodes without causing tissue damage or discomfort for the patient. It can be appreciated that the benefit of having an enclosure to sink/source extra current as needed is even more apparent as the electrode size variations become greater, since current balancing using just the electrode array 210C (and without the enclosure 200C) would have been even more difficult.

Another advantage offered by the mixed mode of operation is prevention of excessive stimulation. For a conventional neurostimulator operating in a strictly monopolar mode, the current level at the enclosure is not programmable. Instead, the amount of current sunk or sourced by the enclosure is the sum of the currents sourced or sunk collectively by the activated electrodes (having the opposite polarity) on the electrode array. Even though the enclosure may have a large surface area, the sum of the currents at the electrodes may still cause discomfort or pain to the patient at the site of the enclosure. The lack of enclosure current programmability means the patient's discomfort or pain cannot be automatically prevented or easily reduced, since often times the clinician or the patient has to manually reprogram the current levels at the electrodes in order to reduce the total amount of current at the enclosure. Until such reprogramming is complete, the patient may suffer from the pain or discomfort due to excessive stimulation at the enclosure site.

In comparison, the neurostimulator herein allows the current at the enclosure to be programmed in a manner similar to other detachable electrodes. This programmability allows algorithms to be developed to automatically prevent patient discomfort or pain. For example, at an initial calibration stage (before the neurostimulator undergoes normal operation), the current level at the enclosure 200C may be slowly ramped up. At some point, the current level will reach a "perception threshold," at which the patient will actually feel a stimulation sensation at the site of the enclosure 200C. The current level corresponding to the perception threshold will be recorded, for example recorded internally at a memory location accessibly by the microcontroller 50 of FIG. 1. The current level may continue to be ramped up until a "pain threshold" is reached, at which the patient will feel pain at the site of the enclosure 200C. The current level corresponding to the pain threshold may also be recorded.

Thereafter, during normal operation of the neurostimulator, the microcontroller 50 may program the distal electrodes and the enclosure in a manner such that the current at the enclosure 200C is capped at a level corresponding to, or slightly lower than, the perception threshold. This may be done for patients who do not want to experience any stimulation sensation at the enclosure site at all. The programming algorithm may also be designed to cap the enclosure current at a level corresponding to, or slightly lower than, the pain threshold. Thus may be done for patients who can tolerate some level of stimulation but do not want to experience any pain at the enclosure site. Any excess amount of current can be programmably diverted to be sourced or sunk by other detachable electrodes 220C-227C on the electrode array 210C.

The current programmability of the enclosure also offers an additional level of safety control. For many conventional neurostimulators, the enclosure is completely passive, in that it is tied to either a power or ground rail. Hence, the enclosure is allowed to source or sink whatever amount of current that is generated by the electrode channels. This configuration may work fine as long as no electrode channels are malfunctioning. However, if one of the electrode channels fails in a manner such that it is providing a high level of current, the passively-used enclosure of a conventional neurostimulator could allow large amounts of current to flow, which may cause patient tissue damage or corrosion at the distal electrode site. In comparison, and as discussed above, the enclosure 200C of the neurostimulator herein can be programmed to have a current output that is always below a predetermined threshold. Thus, even if one or more electrode channels begin to fail, the enclosure would not allow a dangerously high amount of current to flow, thereby providing an additional safety mechanism. In other words, both the current source for the distal electrode and the current source for the enclosure would have to fail for a high current fault to occur.

Another advantage offered by the mixed mode of operation is flexible and more effective stimulation. The mixed mode of operation in effect is a combination of the monopolar mode and the bipolar mode, and as such offers stimulation paths 270-271 and 280-283 that are a collection of stimulation paths associated with the monopolar mode and the bipolar mode. Therefore, the stimulation coverage area of the mixed mode extends beyond the stimulation area of either the monopolar mode or the bipolar mode. For example, in the strictly monopolar mode of operation, the stimulation paths 280-283 would not have been available. Thus, it would have been very difficult for a conventional monopolar neurostimulator to effectively stimulate nerve tissues within or near the stimulation paths 280-283. As another example, in the strictly bipolar mode of operation, the stimulation paths 270-271 would not have been available. Thus, it would have been very difficult for a conventional bipolar neurostimulator to effectively stimulate nerve tissues outside the electrode array 210C.

These shortcomings of strictly monopolar or strictly bipolar neurostimulators are exacerbated if electrodes (or the enclosure itself) shift after implant, which means target nerve tissues may fall outside of originally intended stimulation paths. For example, if the implanted electrode array has migrated beyond the target nerve tissue areas, a conventional bipolar neurostimulator may no longer be able to stimulate the target nerve tissue. Here, in the mixed mode of operation, one or more electrodes 220C-227C may be selectively activated to form one or more stimulation paths in conjunction with the enclosure 200C, which would still offer stimulation coverage of the target nerve tissue. Hence, the mixed mode of operation increases stimulation flexibility and effectiveness through additional stimulation paths. The clinician or patient may be able to stimulate target nerve tissues with more precision and accuracy using the mixed mode neurostimulator according to various aspects of the present disclosure.

Another advantage offered by the mixed mode of operation is more effective pre-biasing of the nerve tissues. The neurostimulator disclosed herein includes features relating to generation of pre-pulses, continuous waveforms, and wave-shaping, which are discussed in more detail in U.S. patent application Ser. No. 13/081,896, Titled "Charge Balancing For Arbitrary Waveform Generator & Neural Stimulation Application" and filed on Apr. 7, 2011, U.S. patent application Ser. No. 13/082,097, Titled "Arbitrary Waveform Generator & Neural Stimulation Application With Scalable Waveform Feature" and filed on Apr. 7, 2011, and U.S. patent application Ser. No. 13/081,936, Titled "Arbitrary Waveform Generator & Neural Stimulation Application" and filed on April 7, each of which is hereby incorporated by reference in its entirety. These features take advantage of the response of the tissue to polarization in order to target specific nerves, thereby providing a distinct advantage over other neurostimulators that do not have these features. For example, pre-pulses (before the stimulation phase) may be utilized to raise or lower the threshold of certain areas of the tissue. The enclosure 200C can be used to accomplish this task in a much larger area, since the enclosure in effect functions as a very large active electrode. In other words, the enclosure 200C herein can be used to carry out tasks such as pre-biasing the tissue more effectively and more efficiently.

Figure 5:
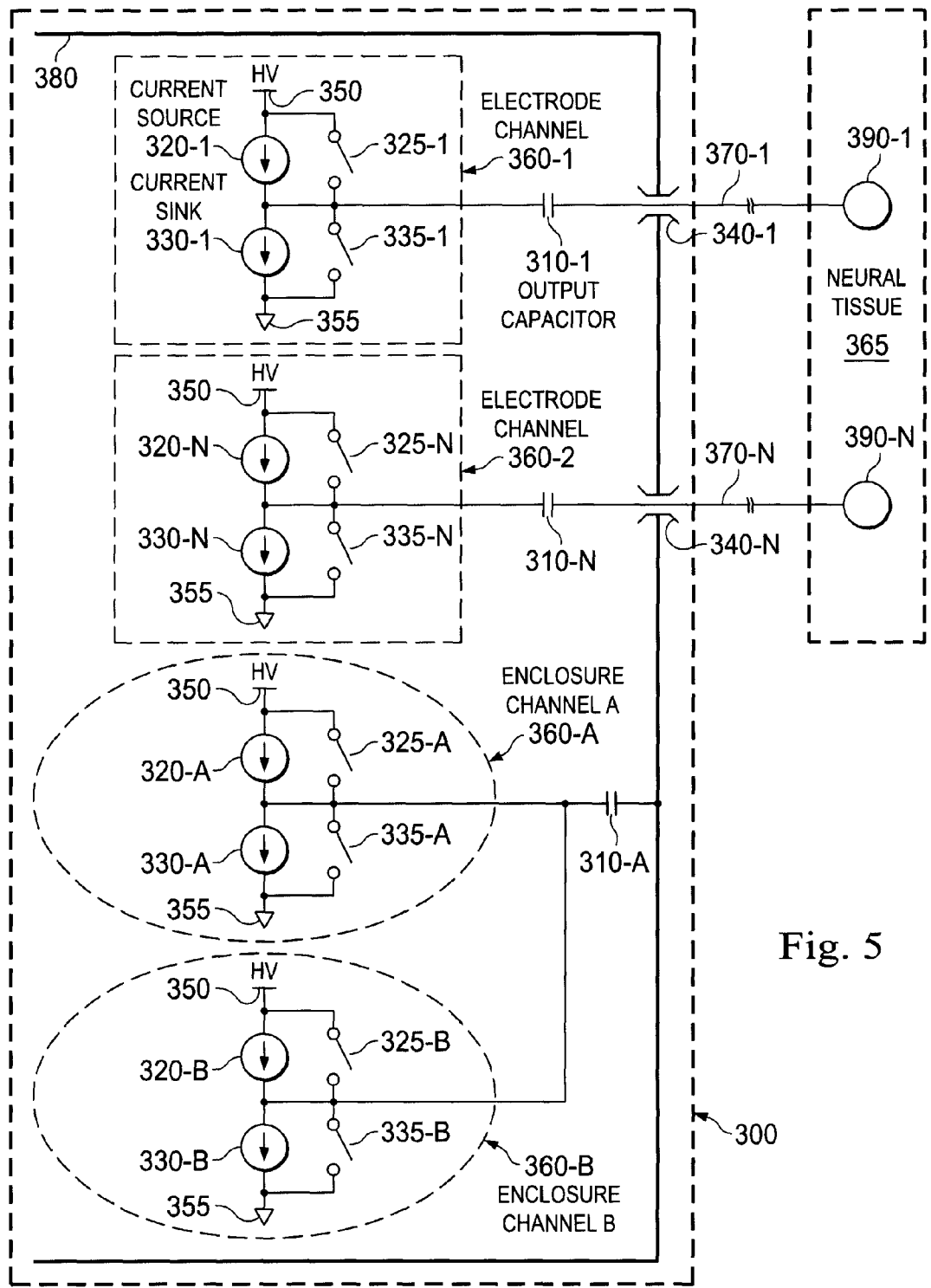
FIG. 5 is a partial view of a stimulation circuit in an implanted pulse generator according to various aspects of the present disclosure.

FIG. 5 is a partial circuit diagrammatic view of a neurostimulator device employing the mixed mode of operation discussed above by actively controlling its enclosure as a programmable electrode. Referring to FIG. 5, stimulation circuitry 300 (an embodiment of the stimulation circuitry 80 of FIG. 1) includes electrode channels 360-1 through 360-N. Each electrode channel 360 may include a respective current source 320, a respective current sink 330, respective switches 325 and 335, power sources 350, and terminals 355 (which may be tied to ground or another electrical reference). The stimulation circuitry 300 may also include a first enclosure channel 360-A and a second enclosure channel 360-B, which can be controlled in a manner that is similar to the electrode channels 360-1 through 360-N.

Current sinks 330 sink electrical current to create an electric field in a target nerve tissue 365. Current sources 320 provide return paths for the current sinks 330. The amount of current (e.g., the current amplitude) sourced or sunk can be programmed through a microcontroller similar to the microcontroller 50 of FIG. 1. Such microcontroller may also control the width (or duration) and frequency of the current pulses. The current sinks 330 and the current sources 320 may collectively be referred to as current supplies. In other embodiments, other types of electrical supplies may be used to generate stimulation pulses to be delivered to distal electrodes. For example, a voltage supply may be used instead of the current supplies shown herein. It is also understood that the current sources 320 and the current sinks 330 are designed and calibrated so that a programmed value will closely match the desired current across all channels.

In each of the electrode channels 360, the switch 325 is coupled in parallel to the current source 320, and the switch 335 is coupled in parallel to the current sink 330. The switches 325 and 335 may be programmably opened or closed. When the switches 325 are programmably closed, they allow the current sources 320 to be electrically bypassed. When the switches 335 are programmably closed, they allow the current sinks 330 to be electrically bypassed. Therefore, the switches 325 and 335 may also be referred to as bypass switches. In actual operation, the switches 325 and 335 may allow uncontrolled current flow to either rail (source or sink) and may be used for passive charge recovery.

Each channel 360 is coupled in series to a respective protective component 310. The protective component 310 shields target nerve tissue 365 from unwanted electrical signals, such as DC signals. A DC component in the electrical stimulation may result in corrosion around the respective electrode contact, causing harm to nearby tissue areas. Consequently, it is desirable for the neurostimulator to filter out any DC component in the electrical signal and deliver only an alternating current (AC) electrical signal to the patient. In the embodiment shown in FIG. 5, protective components 310 are DC-blocking capacitors. The DC-blocking capacitors may have a capacitance ranging from about 0.1 microfarad (μF) to about 5 μF. Other capacitance values may be used for alternative embodiments. These capacitors may also be used for charge-balancing purposes.

The switches 325 and 335, current sources 320 and sinks 330, and protective components 310 are contained within a hermetically-sealed enclosure 380 that is similar to the enclosure 150 (FIG. 1) and the enclosure 200C (FIG. 4) discussed above. The enclosure 380 contains feedthrough mechanisms 340, out of which conductors can extend. Each conductor is coupled to a respective lead wire 370 via a connector on the IPG 300, or may be permanently connected. For each lead wire 370, its proximal end is coupled to a respective protective component 310. The distal end of each lead wire 370 is coupled to a respective electrode 390, a plurality of which are implanted at or near target nerve tissue 365. The electrodes 390 deliver neural stimulation to target nerve tissue 365 through the generation of electrical fields. The strength and duration of the electric field, which determines the level of paresthesia sensation, can be adjusted by changing the amplitude and width of the current pulse at each electrode.

As discussed above, the hermetically-sealed enclosure 380 may also serve as an electrode in a manner similar to the detachable electrodes 390. As illustrated in FIG. 5, the enclosure 380 may be driven with a current source 320-A similar to the current sources 320 and a current sink 330-A similar to current sinks 330. Source 320-A, sink 330-A, and switches 325-A and 335-A may form a first channel 360-A coupled to enclosure 380. Also, it is possible for protective component 310-A to be included as a protective component coupled between the enclosure channel 360-A and the enclosure 380. A second channel 360-B including current source 320-B, current sink 330-B, and switches 325-B and 335-B may also be used to drive the enclosure 380 as well. It is understood that any number of channels 360 may be used to drive the enclosure 380. For example, a single enclosure channel may be used to drive the enclosure 380 in some embodiments, while more than two enclosure channels may be used to drive the enclosure 380 in other embodiments.

For each channel driving the enclosure 380, its respective current source and current sink are designed in the same way as the current sources 320 and the current sinks 330 in channels 360 driving the detachable electrode 390. This allows the enclosure channels to have the same accuracy and resolution as the electrode channels 360-1 through 360-N. Hence, the enclosure channels (such as the channels 360-A and 360-B) can be calibrated and programmed in conjunction with the electrode channels 360-1 through 360-N.

Once again, since the enclosure 380 is actively driven (e.g., by the channels 360-A and 360-B), it is thus operable in the same way as electrodes 390-1 through 390-N, which are actively driven by their respective channels 360-1 through 360-N. Furthermore, although only four channels 360 (360-1, 360-2, 360-A and 360-B) are shown in FIG. 5, it is understood that the stimulation circuitry 300 may contain any number of channels 360. Any one of channels 360 is capable of sinking and sourcing a variable amount of current to stimulate a specific area of target nerve tissue 365, depending on the exact stimulation path created.

In FIG. 5, the current sources 320 and current sinks 330 may be referred to as "bidirectional" current supplies. As discussed above, the amplitude and the polarity of the output of the bidirectional current supplies may be precisely controlled by a microcontroller. Each bidirectional current supply 360 can produce a current amplitude ranging from about −15.0 mA to about +15.0 mA in 15 μA (microamperes, 1 μA=$10^{-6}$ A) steps.

Although embodiments consistent with FIG. 5 utilize bidirectional current supplies (e.g., current sources 320 and current sinks 330), unidirectional current supplies may be used in other embodiments instead. For example, unidirectional current supplies may be implemented in the manner described in detail in U.S. patent application Ser. No. 13/098,071, Titled "CURRENT STEERING NEUROSTIMULATOR DEVICE WITH UNIDIRECTIONAL CURRENT SOURCES" and filed on Apr. 29, 2011, the content of which is hereby incorporated by reference in its entirety.

Figure 6:
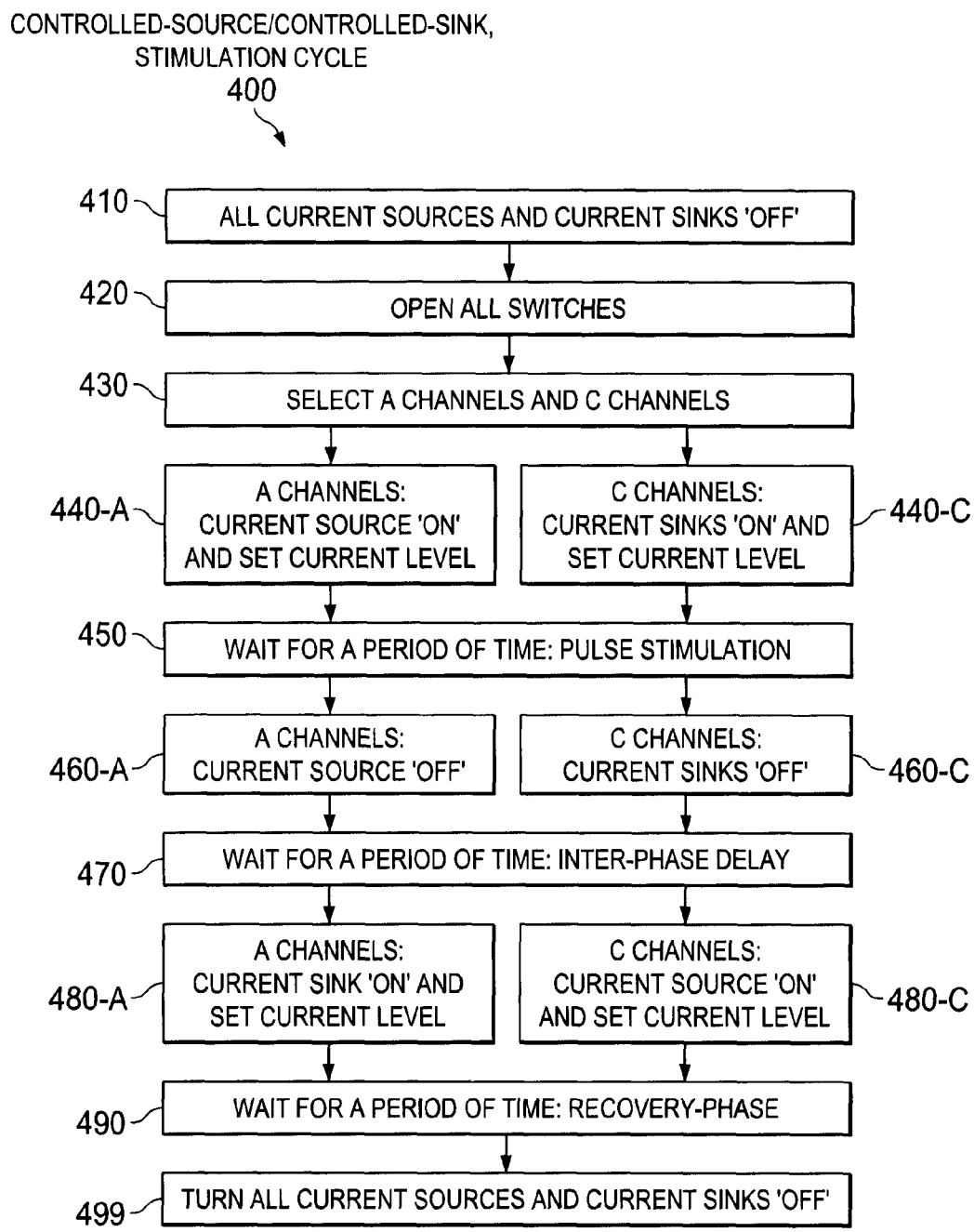
FIG. 6 is a flowchart illustrating a method for using a neurostimulator device according to some embodiments where all currents provided during the stimulation pulse are actively controlled.
Figure 7:
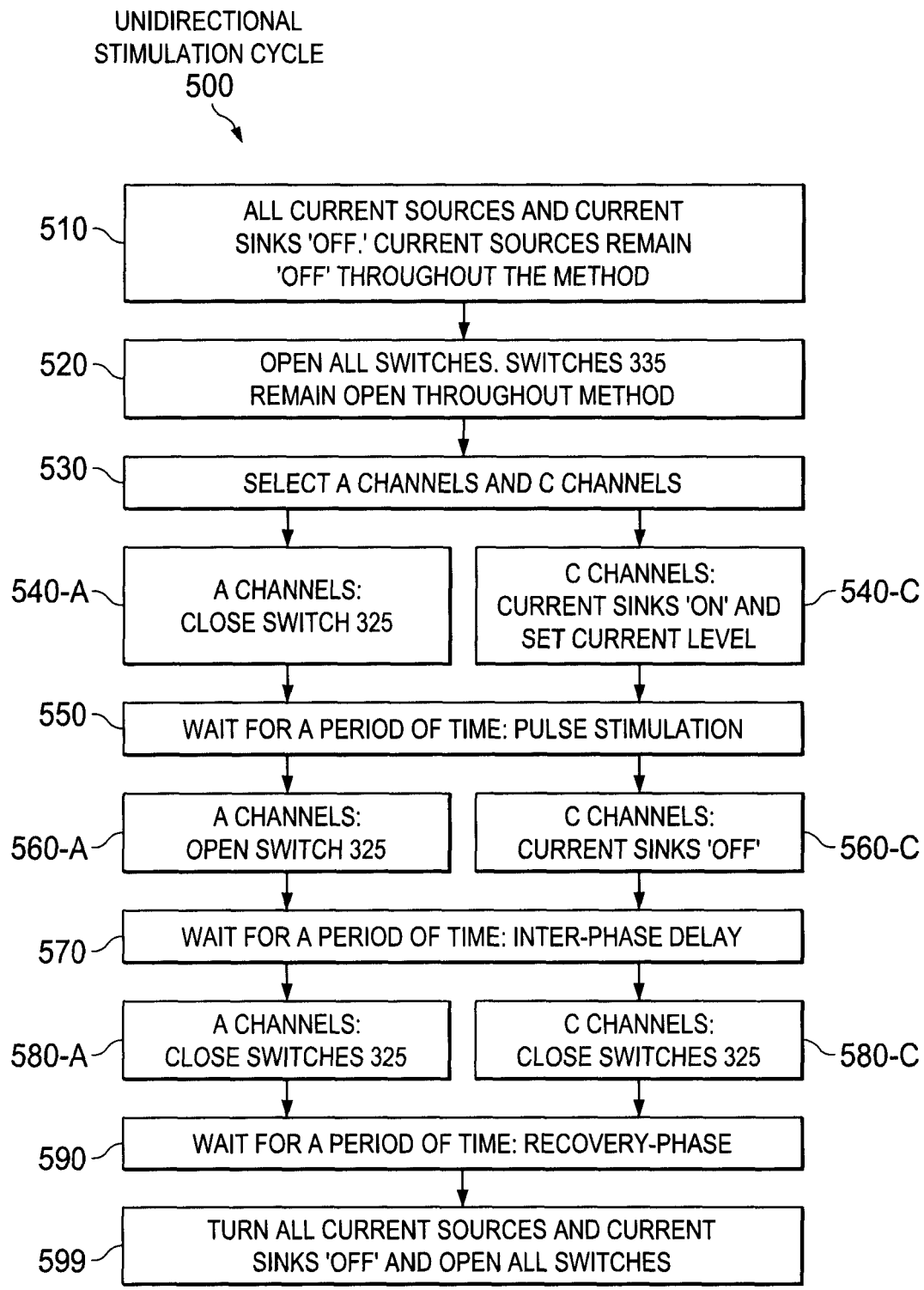
FIG. 7 is a flowchart illustrating a method for using a neurostimulator device according to some embodiments where some currents provided during the stimulation pulse are actively controlled while additional currents are provided in a passive manner.
Figure 8:
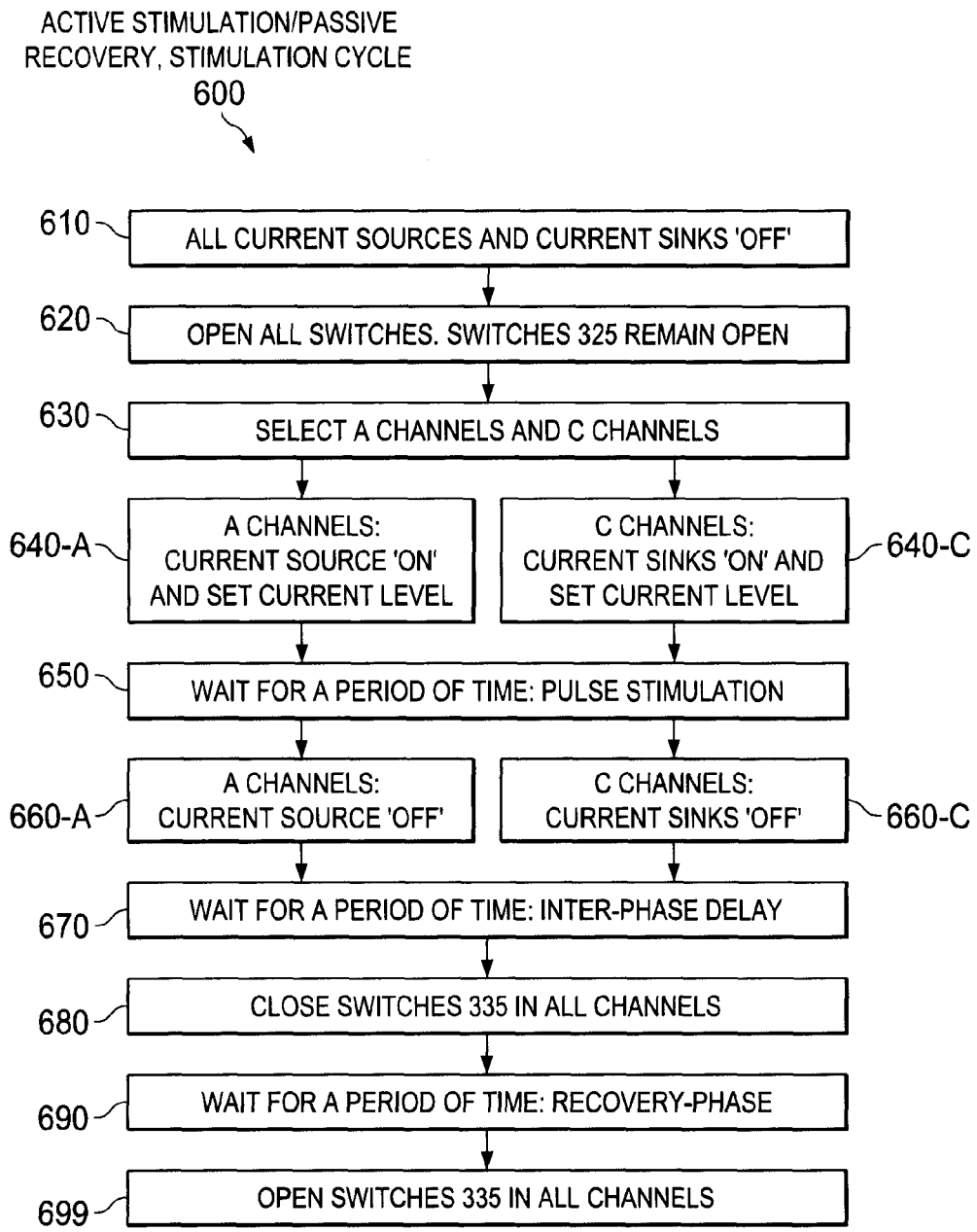
FIG. 8 is a flowchart illustrating a method for using a neurostimulator device according to some embodiments where all currents provided during a first portion of the stimulation pulse are actively controlled while all currents provided during a second portion of the stimulation pulse are provided in a passive manner.

In the following paragraphs, a detailed description of FIGS. 6-8 will be provided. FIGS. 6-8 show flowcharts illustrating embodiments of a method to use a neurostimulator device including an IPG and stimulation circuitry as discussed above with reference to FIGS. 1-5. In general, methods consistent with FIGS. 6-8 for using a neurostimulator device may include a pulse or cycle which is repeated for a number of times. Each pulse or cycle may include a stimulation phase and a recovery phase. According to some embodiments, the stimulation phase is the therapeutic portion of a pulse or continuous waveform. In some embodiments, the recovery phase is a charge-balancing portion of a pulse. The stimulation phase takes place during a pre-selected first period of time, and the recovery phase takes place during a pre-selected second period of time.

FIG. 6 is a flowchart illustrating method 400 for operating a neurostimulator device according to some embodiments. In more detail, the method 400 is a controlled-source/controlled-sink stimulation cycle performed using a device consistent with the neurostimulator discussed above in accordance with various aspects of the present disclosure. The flowchart in FIG. 6 corresponds to a 'pulse stimulation' cycle that may be repeated as many times as necessary. The cycle includes the following steps.

In step 410, all current sources 320 and current sinks 330 are turned off (or stated differently, set to 0 mA). All switches 325 and 335 are opened in step 420. Switches 325 and 335 remain opened throughout all steps in method 400. A set of A-channels 360 is selected from channels 360 in step 430. A-channels will act as 'Anode' (positive) channels in a pulse stimulation stage of method 400. Another set of C-channels 360 is selected from channels 360 also in step 430. C-channels will act as 'Cathode' (negative) channels in a 'pulse stimulation' stage of method 400.

In step 440-A, current sources 320 are turned 'on' and set to the desired stimulation current for that channel, in all A-channels. In step 440-C, current sinks 330 are turned 'on' and set to the desired stimulation current for that channel, in all C-channels. According to some embodiments of method 400, steps 440-A and 440-C are performed simultaneously, or almost simultaneously. In some embodiments, performing of steps 440-A and 440-C takes place within a few tens of nanoseconds from each other. In step 450, a predetermined length of time or 'pulse stimulation' period lapses while electric current is provided by channels 360.

In step 460-A, all current sources 320 in A-channels are turned 'off.' In step 460-C, all current sinks 330 in C-channels are turned 'off.' According to some embodiments of method 400, steps 460-A and 460-C are performed simultaneously, or almost simultaneously. In some embodiments, performing of steps 460-A and 460-C takes place within a few tens of nanoseconds from each other. In step 470 a predetermined length of time or 'inter-phase delay' period lapses while electric current is 'off.'

In step 480-A, current sinks 330 are turned 'on' and set to the desired current levels for that channel, in all A-channels. In step 480-C, current sources 320 are turned 'on' and set to the desired current levels for that channel, in all C-channels. According to some embodiments of method 400, steps 480-A and 480-C are performed simultaneously, or almost simultaneously. In some embodiments, performing of steps 480-A and 480-C takes place within a few tens of nanoseconds from each other. In step 490, a predetermined length of time or 'recovery-phase' period lapses while electric current is provided by channels 360. In some embodiments of method 400, the amplitude of the 'recovery-phase' is chosen so that the amplitude is less than a threshold value.

FIG. 7 is a flowchart illustrating method 500 illustrating an operation of a neurostimulator device according to some embodiments. In more detail, the method 500 is a unidirectional stimulation cycle performed using a device consistent with the neurostimulator discussed above in accordance with various aspects of the present disclosure. The flowchart in FIG. 7 corresponds to a 'pulse stimulation' cycle that may be repeated as many times as necessary. The cycle includes the following steps.

In step 510, all current sources 320 and current sinks 330 are turned 'off' (or alternatively stated, set to 0 mA). Current sources 320 remain 'off' throughout the unidirectional stimulation cycle in method 500. All switches 325 and 335 are opened in step 520. Switches 335 remain open throughout all steps in method 500. A set of A-channels 360 is selected from channels 360 in step 530. A-channels will act as 'Anode' (positive) channels in a 'pulse stimulation' stage of method 500. Another set of C-channels 360 is selected from channels 360 also in step 530. C-channels will act as 'Cathode' (negative) channels in a 'pulse stimulation' stage of method 500.

In step 540-A, switches 325 are closed in all A-channels. In step 540-C current sinks 330 are turned 'on' and set to the desired stimulation current for that channel, in all C-channels. According to some embodiments of method 500, steps 540-A and 540-C are performed simultaneously, or almost simultaneously. In some embodiments, performing of steps 540-A and 540-C takes place within a few tens of nanoseconds from each other. In step 550, a predetermined length of time or 'pulse stimulation' period lapses while electric current is provided by channels 360.

In step 560-A, switches 325 in A-channels are opened. In step 560-C, all current sinks 330 in C-channels are turned 'off.' According to some embodiments of method 500, steps 560-A and 560-C are performed simultaneously, or almost simultaneously. In some embodiments, performing of steps 560-A and 560-C takes place within a few tens of nanoseconds from each other. In step 570, a predetermined length of time or 'inter-phase delay' period lapses while electric current is 'off.'

In step 580-A, switches 325 are closed in all A-channels. In step 580-C, switches 325 are closed in all C-channels. According to some embodiments of method 500, steps 580-A and 580-C are performed simultaneously, or almost simultaneously. In some embodiments, performing of steps 580-A and 580-C takes place within a few tens of nanoseconds from each other. In step 590, a predetermined length of time or 'recovery-phase' period lapses while electric current is provided by channels 360. In some embodiments of method 500, the duration of the 'recovery-phase' period is chosen so that the charge stored in protective component 310 is less than a threshold value. Protective component 310 may be a capacitor, and the threshold value may be attained once a current value close to 0 mA flows through lead 370. The threshold may be determined by a current of a few µA, such as 15 µA, according to some embodiments.

FIG. 8 is a flowchart illustrating method 600 for using a neurostimulator device according to some embodiments. In more detail, the method 600 is an active-stimulation/passive recovery stimulation cycle, performed using a device consistent with the neurostimulator discussed above in accordance with various aspects of the present disclosure. The flowchart in FIG. 8 corresponds to a 'pulse stimulation' cycle that may be repeated as many times as necessary. The cycle includes the following steps.

In step 610, all current sources 320 and current sinks 330 are turned 'off' (or equivalently, set to 0 mA). All switches 325 and 335 are opened in step 620. Switches 325 remain open throughout all steps in method 600. A set of channels 360 (A-channels) is selected from channels 360 in step 630. A-channels will act as 'Anode' (positive) channels in a 'pulse stimulation' stage of method 600. Another set of channels 360 (C-channels) is selected from channels 360 also in step 630. C-channels will act as 'Cathode' (negative) channels in a 'pulse stimulation' stage of method 600.

In step 640-A, current sources 320 are turned 'on' and set to a desired stimulation current for that channel, in all A-channels. In step 640-C, current sinks 330 are turned 'on' and set to the desired stimulation current for that channel, in all C-channels. According to some embodiments of method 600, steps 640-A and 640-C are performed simultaneously, or almost simultaneously. In some embodiments, performing of steps 640-A and 640-C takes place within a few tens of nanoseconds from each other. In step 650, a predetermined length of time or 'pulse stimulation' period lapses while electric current is provided by channels 360.

In step 660-A, all current sources 320 in A-channels are turned 'off.' In step 660-C, all current sinks 330 in C-channels are turned 'off.' According to some embodiments of method 600, steps 660-A and 660-C are performed simultaneously, or almost simultaneously. In some embodiments, performing of steps 660-A and 660-C takes place within a few tens of nanoseconds from each other. In step 670, a predetermined length of time or 'inter-phase delay' period lapses while electric current is 'off.'

In step 680, switches 335 are closed in all channels 360. In step 690, a predetermined length of time or 'recovery-phase' period lapses. In some embodiments of method 600, the duration of the 'recovery-phase' period is chosen so that the charge stored in protective component 310 is less than a threshold value. Protective component 310 may be a capacitor, and the threshold value may be attained once a current value close to 0 mA flows through channel 370. For example, the threshold may be obtained once a current of less than a few µA flows through channel 370, such as 15 µA according to some embodiments.

Figure 9:
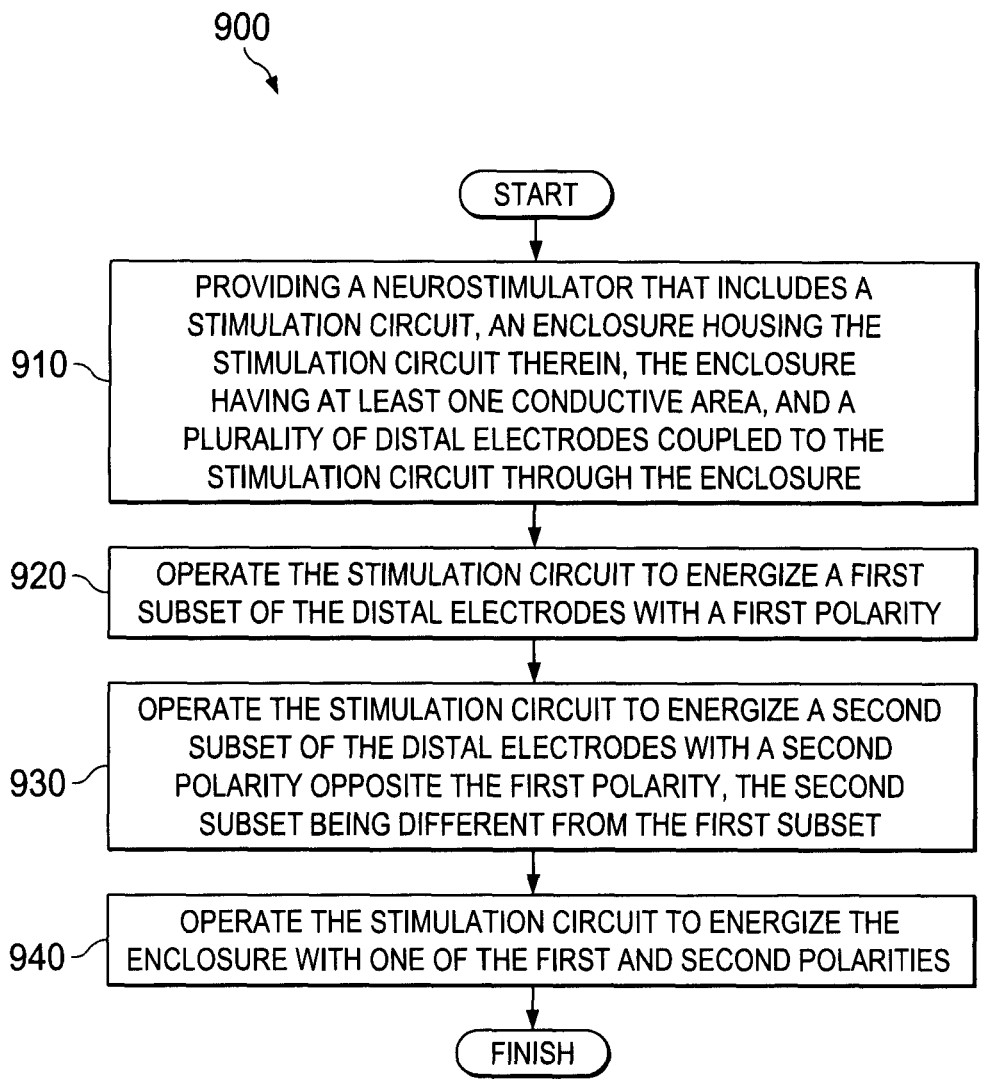
FIG. 9 is a flowchart illustrating a method involving an operation of the neurostimulator device according to various aspects of the present disclosure.

FIG. 9 illustrates a flowchart of a method 900 involving the neurostimulator device 20. The method 900 contains a plurality of blocks 910-940. It is understood that the blocks 910-940 are not necessarily sequentially executed in a manner as shown in FIG. 9. Rather, the execution of the blocks 910-940 may be done simultaneously or in a different sequence. Further, it is understood that the blocks 910-940 pertain to setting up a stimulation pulse, not the execution of the stimulation pulse. The method 900 includes a block 910, in which a neurostimulator is provided. The neurostimulator includes a stimulation circuit and an enclosure that houses the stimulation circuit therein. The enclosure has at least one conductive area. The neurostimulator includes a plurality of distal electrodes coupled to the stimulation circuit through the enclosure. The method 900 includes a block 920, in which the stimulation circuit is operated to energize a first subset of the distal electrodes with a first polarity. The method 900 includes a block 930, in which the stimulation circuit is operated to energize a second subset of the distal electrodes with a second polarity opposite the first polarity, the second subset being different from the first subset. The method 900 includes a block 940, in which the stimulation circuit is operated to energize the enclosure with one of the first and second polarities.

Figure 10B:
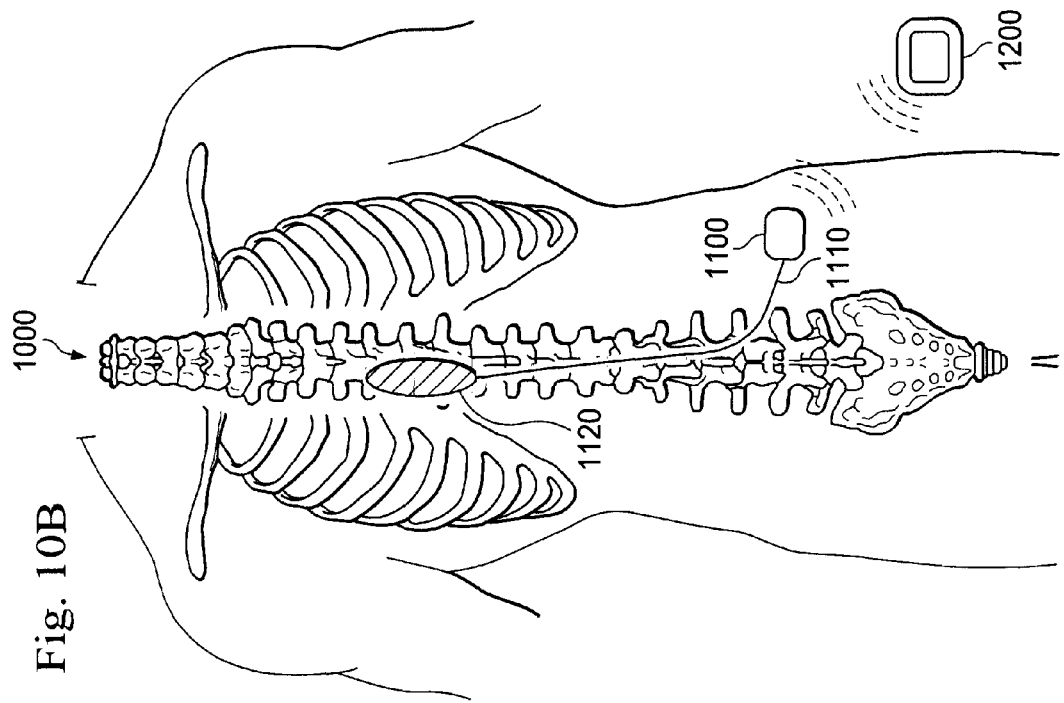
FIGS. 10A and 10B are side and posterior views of a human spine, respectively.
Figure 10A:
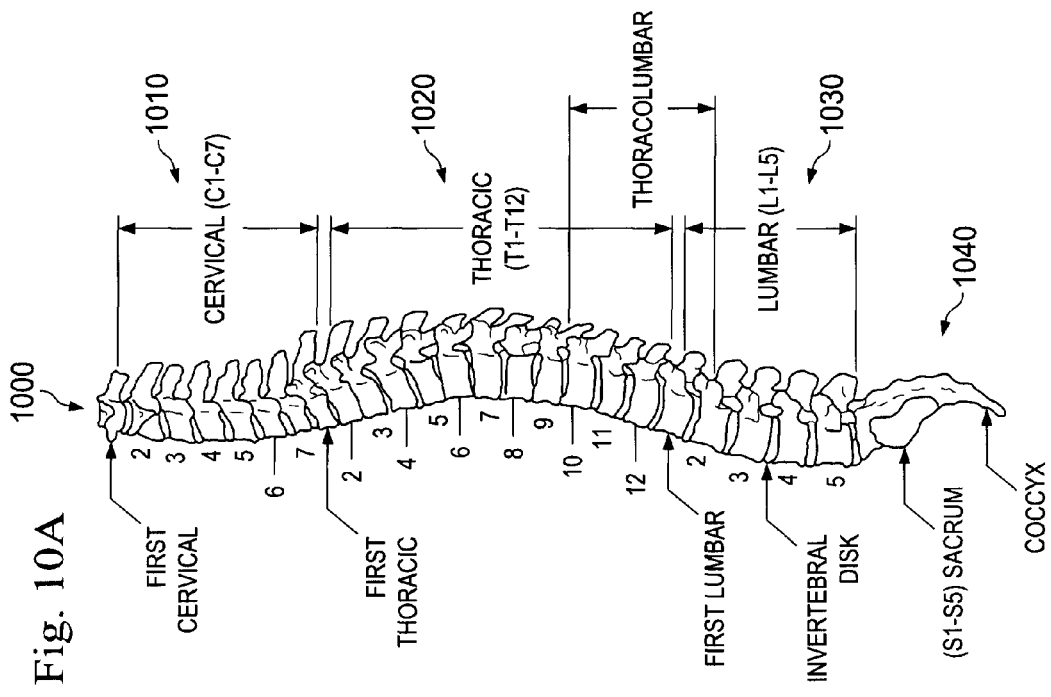

FIG. 10A is a side view of a spine 1000, and FIG. 10B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 10B, an IPG device 1100 is implanted inside the body. The IPG device 1100 may include various embodiments of the neurostimulator device 20 described above. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator as described above may be placed in different locations throughout the body and may be programmed to address a variety of problems, including for example but without limitation; prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A neurostimulation medical system, comprising:
a controller circuit configured to generate control signals in response to external programming signals;
a stimulation circuit configured to generate stimulation signals in response to the control signals;
a plurality of implantable electrodes;
a plurality of conductors configured to deliver the stimulation signals from the stimulation circuit to the electrodes; and
an enclosure that houses the controller circuit and the stimulation circuit therein, the enclosure containing an area that is electrically conductive, wherein the controller circuit and the stimulation circuit are configured to ramp up a current at the enclosure during an initial calibration stage and determine therefrom a first current level corresponding to a perception threshold at the enclosure and a second current level corresponding to a pain threshold at the enclosure;
wherein the stimulation circuit is configured to activate a first subset of the electrodes to a first polarity, a second subset of the electrodes to a second polarity, and the enclosure to one of the first and second polarities, so as to cause a first stimulation path to be formed between at least one of the electrodes in the first subset and at least one of the electrodes in the second subset, and a second stimulation path to be formed between the enclosure and at least one of the electrodes in the first and second subsets, and wherein the activated enclosure is programmed by the controller circuit to actively sink or source an amount of electrical current that is capped at one of: the first current level corresponding to the perception threshold, and the second current level corresponding to the pain threshold.

2. The neurostimulation medical system of claim 1, wherein the electrodes in the first subset are activated as anodes, and the electrodes in the second subset are activated as cathodes, and the enclosure is activated as one of: an anode and a cathode.

3. The neurostimulation medical system of claim 1, wherein the stimulation circuit includes a plurality of stimulation channels that can be selectively activated in response to the control signals, wherein the stimulation channels each include an electrical current source.

4. The neurostimulation medical system of claim 3, wherein a number of activated stimulation channels is equal to X, and a number of activated distal electrodes is equal to Y, and wherein X is greater than Y.

5. The neurostimulation medical system of claim 1, wherein the amount of electrical current at the enclosure is capped at the first current level corresponding to the perception threshold.

6. The neurostimulation medical system of claim 5, wherein the current source contains a current supply for generating current pulses that can be used as the stimulation signals, wherein an amplitude, a width, and a frequency of the current pulses are each tunable in response to the control signals.

7. The neurostimulation medical system of claim 1, wherein the enclosure is a hermetically-sealed device, and wherein the stimulation circuit activates the enclosure through the area that is electrically conductive, and wherein the stimulation circuit activates the enclosure using one or more dedicated current sources.

8. A neurostimulation medical system, comprising:
a controller circuit configured to generate control signals in response to external programming signals;
a stimulation circuit configured to generate stimulation signals in response to the control signals;
a plurality of distal electrodes;
a plurality of conductors configured to deliver the stimulation signals from the stimulation circuit to the electrodes; and
an enclosure that houses the controller circuit and the stimulation circuit therein, the enclosure containing at least one electrically conductive area, wherein the distal electrodes are coupled to the stimulation circuit through the enclosure, wherein the controller circuit and the stimulation circuit are configured to ramp up a current at the enclosure during an initial calibration stage and determine therefrom a first current level corresponding to a perception threshold at the enclosure and a second current level corresponding to a pain threshold at the enclosure;
wherein the stimulation circuit is configured to:
energize a first subset of the distal electrodes with a first polarity;
energize a second subset of the distal electrodes with a second polarity opposite the first polarity, the second subset being different from the first subset; and
energize the enclosure with one of the first and second polarities, and wherein the energized enclosure is programmed by the controller circuit to actively sink or source an amount of electrical current that is capped at one of: the first current level corresponding to the perception threshold, and the second current level corresponding to the pain threshold.

9. The neurostimulation medical system of claim 8, wherein the stimulation circuit is configured by a microcontroller that is a part of the controller circuit.

10. The neurostimulation medical system of claim 8, wherein the stimulation circuit is configured to energize the first and second subsets of distal electrodes and the enclosure simultaneously, wherein the first and second subsets of distal electrodes and the enclosure are energized with a controlled electrical current.

11. The neurostimulation medical system of claim 8, wherein the amount of electrical current at the enclosure is capped at the first current level corresponding to the perception threshold.

12. The neurostimulation medical system of claim 8, wherein the neurostimulation medical system includes a plurality of stimulation channels that can be driven by the stimulation circuit, each stimulation channel having one or more programmable electrical supplies configured to supply stimulation signals to the distal electrodes.

13. The neurostimulation medical system of claim 12, wherein a number of stimulation channels that can be driven exceeds a sum of the energized distal electrodes.

14. The neurostimulation medical system of claim 8, wherein the neurostimulation medical system includes a charge-balancing capacitor.

15. The neurostimulation medical system of claim 8, wherein the neurostimulation medical system is implantable in a patient's body.

16. The neurostimulation medical system of claim 8, wherein the stimulation circuit is further configured to:
    energize a third subset of the distal electrodes with the first polarity; and
    energize a fourth subset of the distal electrodes with the second polarity, wherein the third and fourth subsets include different electrodes than the first and second subsets, respectively.

17. The neurostimulation medical system of claim 16, wherein an amount of stimulation current flowing through the enclosure while the first and second subsets are energized is different from an amount of stimulation current flowing through the enclosure while the third and fourth subsets are energized.

18. A neurostimulation medical system, comprising:
    a controller circuit configured to generate control signals in response to external programming signals;
    a stimulation circuit configured to generate stimulation signals in response to the control signals;
    a distal electrode array that is implantable in a human body;
    a plurality of conductors configured to deliver the stimulation signals from the stimulation circuit to the electrodes; and
    a housing component that houses the stimulation circuit therein, the housing component containing at least one electrically conductive area, wherein the controller circuit and the stimulation circuit are configured to ramp up a current at the housing component during an initial calibration stage and determine therefrom a first current level corresponding to a perception threshold at the housing component and a second current level corresponding to a pain threshold at the housing component; wherein:
    the stimulation circuit includes a plurality of controllable stimulation channels, a first subset of the stimulation channels being electrically coupled to the conductors, and a second subset of the stimulation channels being electrically coupled to the electrically conductive area of the housing component; and
    the stimulation circuit is operable to simultaneously create a first stimulation path in the electrode array and a second stimulation path that extends from the electrode array to the housing component, and wherein the housing component, while functioning as a part of the second subset of the stimulation channels, actively sinks or sources a programmed amount of electrical current that is capped at one of: the first current level corresponding to the perception threshold and the second current level corresponding to the pain threshold.

19. The neurostimulation medical system of claim 18, wherein the stimulation channels each include at least one electrical supply for delivering a stimulation signal to the electrode array, and wherein the stimulation channels each further include:
    a programmable switch coupled in parallel with the electrical supply; and
    a capacitor coupled in series with the electrical supply and between the electrical supply and a respective one of the conductors.

20. The neurostimulation medical system of claim 18, wherein the programmed amount of electrical current at the housing component is capped at the first current level corresponding to the perception threshold.

21. The neurostimulation medical system of claim 18, wherein the stimulation channels each include at least one of: a current sink and a current source.

22. The neurostimulation medical system of claim 18, wherein:
    the electrode array contains a first number of activated distal electrodes;
    the stimulation circuit includes a second number of active stimulation channels; and
    the first number is less than the second number.

23. The neurostimulation medical system of claim 22, wherein:
    the first stimulation path is defined by a first distal electrode and a second distal electrode, the first and second distal electrodes being distal electrodes on the distal electrode array and having opposite polarities; and
    the second stimulation path is defined by one of the first and second electrodes and the conductive area of the housing component, the one of the first and second electrodes and the housing component having opposite polarities.

24. The neurostimulation medical system of claim 18, wherein the housing component is a hermetically-sealed enclosure having one or more feedthroughs for receiving the plurality of conductors.

25. A neurostimulation medical system, comprising:
    a controller circuit configured to generate control signals in response to external programming signals;
    a stimulation circuit configured to generate stimulation signals in response to the control signals, wherein the stimulation circuit contains a plurality of current sources, and wherein at least a subset of the current sources each include at least one adjustable electrical supply;
    a plurality of implantable distal electrodes;
    a lead wire coupling assembly for electrically coupling the stimulation circuit to the distal electrodes; and
    an enclosure that houses the stimulation circuit therein, the enclosure having at least one electrically conductive portion, wherein at least one of the current sources in the subset is electrically coupled to the electrically conductive portion of the enclosure, wherein the controller circuit and the stimulation circuit are configured to ramp up a current at the enclosure during an initial calibration stage and determine therefrom a first current level corresponding to a perception threshold at the enclosure and a second current level corresponding to a pain threshold at the enclosure, and wherein the enclosure is programmed by the controller circuit to actively sink or source an amount of electrical current that is capped at one of: the first current level and the second current level.

26. The neurostimulation medical system of claim 25, wherein a quantity of current sources exceeds a quantity of distal electrodes.

27. The neurostimulation medical system of claim 25, wherein the stimulation circuit is configured to drive the enclosure to serve as one of: an anode and a cathode, and wherein the amount of electrical current at the enclosure is capped at the first current level.

28. The neurostimulation medical system of claim 25, wherein the stimulation circuit is configured to simultaneously drive a first subset of the distal electrodes to a first polarity, a second subset of the distal electrodes to a second polarity opposite the first polarity, and the enclosure to one of the first and second polarities.

29. The neurostimulation medical system of claim 28, wherein:
a first stimulation region is formed between one of the distal electrodes in the first subset and one of the distal electrodes in the second subset; and
a second stimulation region is formed between the enclosure and one of the distal electrodes in the first and second subsets.

30. The neurostimulation medical system of claim 25, wherein the electrical supply includes at least one of: a current sink and a current source.

31. A neurostimulation medical system, comprising:
a controller circuit configured to generate control signals in response to external programming signals;
a stimulation circuit configured to generate stimulation signals in response to the control signals;
a remote electrode array;
a plurality of lead wires configured to provide electrical pulses generated by the stimulation circuit to the remote electrode array; and
an enclosure that surrounds the stimulation circuit, the enclosure containing at least one electrically conductive area, wherein the lead wires are coupled to the stimulation circuit through the enclosure, wherein the controller circuit and the stimulation circuit are configured to ramp up a current at the enclosure during an initial calibration stage and determine therefrom a first current level corresponding to a perception threshold at the enclosure and a second current level corresponding to a pain threshold at the enclosure;
wherein the stimulation circuit is configured to:
cause a first stimulation path to be formed within the remote electrode array; and
cause a second stimulation path to be formed from the remote electrode array to the enclosure;
wherein the enclosure is programmed to actively sink or source an amount of electrical current that is capped at one of: the first current level corresponding to the perception threshold, and the second current level corresponding to the pain threshold.

32. The neurostimulation medical system of claim 31, wherein the first stimulation path and the second stimulation path each include a current path, and wherein the stimulation circuit is configured to cause the first and second stimulation paths to be formed simultaneously.

33. The neurostimulation medical system of claim 31, wherein the amount of electrical current at the enclosure is capped at the first current level corresponding to the perception threshold.

34. The neurostimulation medical system of claim 31, wherein the electrode array contains a plurality of electrodes, and wherein the stimulation circuit is configured to:
activate at least one cathode from the plurality of electrodes;
activate at least one anode from the plurality of electrodes; and
activate the enclosure to function in a manner similar to one of: a cathode and an anode.

35. The neurostimulation medical system of claim 34, wherein:
the first stimulation path includes a first stimulation current that passes from one of the activated cathodes to one of the activated anodes; and
the second stimulation path includes a second stimulation current that passes from the enclosure to one of the activated cathodes and anodes.

36. The neurostimulation medical system of claim 31, wherein the stimulation circuit includes a plurality of output channels, the output channels each containing:
a power rail;
a reference voltage;
one or more controllable current supplies;
a first switch coupled to the power rail; and
a second switch coupled to the reference voltage;
wherein:
a first controllable current supply is coupled to the power rail in parallel with the first switch; and
a second controllable current supply is coupled to the reference voltage in parallel with the second switch.

37. The neurostimulation medical system of claim 36, wherein the stimulation circuit is configured to:
turn 'off' all current through the output channels;
open the first switch and the second switch in all output channels;
select a set of anode channels and a set of cathode channels from the output channels;
turn 'on' the first controllable current supply, setting the current to a pre-selected value, and provide current for a first period of time in the anode channels;
turn 'on' the second controllable current supply, setting the current to a pre-selected value, and providing current for the first period of time in the cathode channels;
turn 'off' all current supplies in the anode channels and the cathode channels for a second period of time;
close the second switch in the anode channels and the cathode channels; and
keep the second switch in the anode channels and the cathode channels closed for a third period of time.

38. A neurostimulation medical system, comprising:
a controller circuit configured to generate control signals in response to external programming signals;
a stimulation circuit configured to generate stimulation signals in response to the control signals, wherein the stimulation signals can stimulate a body tissue, and wherein the stimulation circuit includes one or more adjustable electrical supplies;
one or more distal electrodes;
a coupling mechanism configured to electrically couple the stimulation circuit to the one or more distal electrodes; and
an enclosure that houses the stimulation circuit therein, the enclosure containing at least one electrically conductive portion, wherein the controller circuit and the stimulation circuit are configured to ramp up a current at the enclosure during an initial calibration stage and determine therefrom a first current level corresponding to a perception threshold at the enclosure and a second current level corresponding to a pain threshold at the enclosure;
wherein the stimulation circuit is configured to simultaneously drive the enclosure through the conductive portion and drive at least a subset of the distal electrodes, wherein the driven enclosure is programmed to actively sink or source an amount of electrical current that is capped at one of: the first current level and the second current level.

39. The neurostimulation medical system of claim 38, wherein the stimulation circuit includes a plurality of channels that each contain:

at least one of the adjustable electrical supplies;
means for bypassing the electrical supplies; and
means for providing charge-balancing.

40. The neurostimulation medical system of claim 38, wherein the electrical supplies of the stimulation circuit are adjustable in response to the external programming signal, and wherein the amount of electrical current at the enclosure is capped at the first current level.

41. The neurostimulation medical system of claim 38, wherein the stimulation circuit is configured to simultaneously energize a first subset of the distal electrodes with a first polarity, a second subset of the distal electrodes with a second polarity opposite the first polarity, and the enclosure with one of the first and second polarities.

42. The neurostimulation medical system of claim 38, wherein the stimulation circuit is configured to simultaneously cause:
 a first stimulation field to be formed between at least two of the distal electrodes; and
 a second stimulation field to be formed between the enclosure and one of the distal electrodes.

\* \* \* \* \*